United States Patent [19]

Clausen et al.

[11] Patent Number: 5,279,313
[45] Date of Patent: Jan. 18, 1994

[54] TWO COMPONENT COMPOSITION AND METHOD FOR BLEACHING HAIR

[75] Inventors: Thomas Clausen; Wolfgang R. Balzer, both of Alsbach, Fed. Rep. of Germany

[73] Assignee: Wella Aktiengesellschaft, Darmstadt, Fed. Rep. of Germany

[21] Appl. No.: 777,544

[22] PCT Filed: Jun. 6, 1991

[86] PCT No.: PCT/EP91/01042

§ 371 Date: Dec. 12, 1991

§ 102(e) Date: Dec. 12, 1991

[87] PCT Pub. No.: WO92/03120

PCT Pub. Date: Mar. 5, 1992

[30] Foreign Application Priority Data

Aug. 18, 1990 [DE] Fed. Rep. of Germany ........ 4026235

[51] Int. Cl.$^5$ ................................................ A61K 7/13
[52] U.S. Cl. ..................................... 132/208; 424/62; 424/70
[58] Field of Search .................. 132/204, 208, 209; 424/62, 70, 71, 72; 8/405, 406, 407; 252/102, 117

[56] References Cited

U.S. PATENT DOCUMENTS

| | | | |
|---|---|---|---|
| 3,378,444 | 4/1968 | Swanson | 424/62 |
| 3,726,967 | 4/1973 | Vorsatz et al. | 424/62 |
| 3,899,288 | 8/1975 | Galerne | 424/70 |
| 3,961,634 | 6/1976 | Busch | 132/208 |
| 3,977,826 | 8/1976 | Iscowitz | 8/111 |
| 4,138,478 | 2/1979 | Reese et al. | 8/406 |
| 4,371,517 | 2/1983 | Vanlerberghe et al. | 424/70 |
| 4,685,931 | 8/1987 | Schieferstein et al. | 8/407 |
| 4,983,315 | 1/1991 | Glogowski et al. | 252/102 |
| 5,077,040 | 12/1991 | Bergmann et al. | 424/70 |
| 5,173,085 | 12/1992 | Brown et al. | 8/406 |

Primary Examiner—Gene Mancene
Assistant Examiner—Frank A. LaViola
Attorney, Agent, or Firm—Michael J. Striker

[57] ABSTRACT

A preparation for use in a hair bleaching composition consists of 30 to 65% by weight of a persulfate granulate having granule diameters from 0.1 to 0.6 cm and at least one other granulated substance including 15 to 45% by weight of granulated alkaline reacting alkali metal salts. The other granulated substance also has particle diameters from about 0.1 to 0.6 cm. It can also contain 0.1 to 3% by weight of a chelating agent, 0.1 to 15% by weight of an anionic, cationic or nonionic surfactant and a water-soluble thickener. The two component composition contains an aqueous solution which is 4 to 18% by weight hydrogen peroxide and the preparation containing the granulated persulfate. Prior to application on the hair the hydrogen peroxide solution is mixed with the preparation.

13 Claims, No Drawings

TWO COMPONENT COMPOSITION AND METHOD FOR BLEACHING HAIR

BACKGROUND OF THE INVENTION

Oxidizing preparations are used for decoloring and bleaching hair. These preparations usually comprise a bleaching powder (powder mixture of inorganic persalts, e.g. sodium or ammonium persulfate, with) on the one hand and an aqueous hydrogen peroxide solution on the other hand.

During application, the bleaching powder is stirred with the aqueous hydrogen peroxide solution. In so doing, a cream or paste which is capable of being applied and is not runny is obtained due to the contained thickening ingredients. The formulations must have a pH value between 8 and 11.5, preferably between 9 and 10, to effect a sufficient bleaching action.

Since commonly used hydrogen peroxide solutions are adjusted so as to be strongly acidic for the purpose of stabilization, the bleaching powder contains a large proportion of alkaline reacting, e.g. sodium carbonate or sodium silicate. When mixing bleaching powder and peroxide solution the pH value is adjusted to the desired range on the one hand due to the and ammonia is released from the ammonium salts contained in the formulation on the other hand, which ammonia causes a swelling of the hair and accordingly a strengthening of the bleaching action.

However, these preparations for producing bleaching agents in the form of powder mixtures have grave disadvantages. For example, separation can occur when using components having different densities because the heavy particles can deposit on the lower portion of the container when transported or stored. As a result, the powder removed from the bottom portion does not have the same chemical composition as that removed from the top portion and has a different bleaching effect.

Separation can be avoided to a great extent through the use of powder mixtures with very small grain sizes. However, these fine powders have the disadvantage that they tend to develop dust extremely easily. Dust develops particularly when opening the container, but to an even greater extent when removing the required amount, which is usually accomplished with a measuring spoon, and also when agitating the ready-to-use formulation. The release of fine dust can lead to irritation of the respiratory organs, particularly as a result of the utilized persulfates. Further, the powder mixtures have a large surface as a result of the small size of the particles, which can lead to a higher absorption of moisture when opening and closing the container and to a deactivation of the bleaching action.

To solve this problem it is suggested in DE-OS 20 23 922 to change the components of the powder mixture into granule form with a water-soluble polymer. As described in DE-OS 20 23 922, this method leads to a loss of ammonia when using aqueous solvent for the polymer. To compensate for this loss it is suggested to increase the content of ammonium salts in the powder mixture. Of course, the loss of ammonia during technical production of the described granules is very difficult to keep constant, so that the chemical composition of the granules produced according to this method fluctuates.

SUMMARY OF THE INVENTION

It is an object of the present invention to provide a preparation in solid form for the production of a composition for decoloring and bleaching the hair which avoids the described disadvantages and nevertheless enables a high and reproducible degree of brightening.

In this respect, it has now been found that this problem is solved in an outstanding manner by a preparation in solid form containing an inorganic persulfate characterized in that the persulfate is in granulated form. The preparation in solid form can either consist of the persulfate granules exclusively or can contain other substances in solid form, e.g. as powder or granules, in addition to the persulfate granules. The preparation according to the invention preferably has a mixture of the persulfate granules and granulated solid substances which are usually contained, particularly the alkaline reacting alkali metal salts or salts of alkaline earth metal. The diameters of the granule particles of the granulated mixture are preferably of approximately identical magnitude.

The quantity of persulfate contained in the preparation is 30 to 65 percent by weight, preferably 40 to 60 percent by weight, when the mixture contains the alkaline reacting alkali metal salts or salts of alkaline earth metal and possibly other solid ingredients.

The production of the persulfate granulation can be effected in that aqueous solutions of the persulfates, which can also contain additions of wetting agents, emulsifiers or water-soluble thickeners, are changed into solid form by spray drying and also in that the persulfates in solid form are granulated by spraying with an aqueous solution of wetting agents, emulsifiers or thickeners, e.g. according to the "rolling drum process". The water content is adjusted by subsequent drying to below 2 percent by weight, preferably below 1 percent by weight.

The diameter of the granule particles contained in the present preparation should be 0.1 to 0.6 cm, preferably 0.2 to 0.4 cm.

The preparation preferably contains, in addition, alkaline reacting alkali metal salts or salts of alkaline earth metal, e.g. sodium silicate, sodium carbonate, sodium hydrogen carbonate or magnesium carbonate, particularly in a total concentration of 15 to 45 percent by weight, preferably 25 to 40 percent by weight, with reference to the total amount of the preparation. Moreover, it can contain chelation reagents for heavy metals, e.g. salts of ethylenediaminetetraacetic acid, in a concentration of 0.1 to 3 percent by weight, preferably 0.5 to 1.5 percent by weight, as well as dyes from the classes of ultramarine dyestuffs or acidic dyestuffs in concentrations of up to 1 percent by weight. The aforementioned substances can be contained in the preparation either in commercially available form as powder or also as granules. The granules can be a mixture of granules of the individual substances or a granulation of the finished mixture. The production of these granulations is effected in a manner corresponding to the production of the persulfate granulations. Auxiliary substances such as wetting agents, emulsifiers or water-soluble thickeners can also be contained.

Substances from the classes of anionic, cationic or nonionic surface-active substances, e.g. fatty alcohol sulfates, ethoxylated fatty alcohol sulfates, alkyl sulfates, alkylbenzenesulfonates, alkyltrimethylammonium salts, alkyl betaines, ethoxylated fatty alcohols, ethoxylated nonylphenols, fatty acid alkanol amides or ethoxylated fatty acid esters are suitable as wetting agents or emulsifiers. They can be contained in a concentration of 0.1 to 15 percent by weight, preferably 0.1 to 7 percent by weight.

Particularly suitable water-soluble thickeners are cellulose ether, e.g. methyl cellulose, ethyl cellulose, hydroxyethyl cellulose, methylhydroxyethyl cellulose, methylhydroxypropyl cellulose or carboxymethyl cellulose, starches such as cornstarch, starch ether such as carboxymethyl starch, hydroxyethyl starch or methyl starch. Also, thickeners such as guar gum, xanthan gum or alginates can be contained. The total concentration of water-soluble thickeners is 0.1 to 15 percent by weight, preferably 1 to 10 percent by weight.

The persulfate granulation has a sufficient resistance to abrasion to prevent the development of dust during storage, removal and application. The separate use of granules of persulfates and the other ingredients has the further advantage that, depending on the mixture ratio, products with different persulfate contents can be produced which also enable different degrees of brightening.

Separation can be avoided by appropriate selection of the grain size of the granulation in question or by adjusting a determined bulk density.

The subject matter of the invention is further a composition for decoloring and bleaching hair having two components. The first component (A) is in solid form and contains an inorganic persulfate and the second component (B) is an aqueous solution containing 4 to 18 percent by volume of hydrogen peroxide, characterized in that component (A) is a preparation described in the preceding in which persulfate is present in granulated form.

The application of the composition according to the invention is effected in that a quantity of component (A) sufficient for bleaching hair, preferably 20 g to 40 g particularly 30 g, is mixed, e.g. by stirring in a dish, immediately prior to use with component (B) whose content of hydrogen peroxide is 4 to 18 percent by volume, preferably 6 to 12 percent by volume, in a weight ratio of 2:1 to 1:3, preferably 1:1.5 to 1:2. A bleaching compound which is thickened when thickeners are used in component (A) is obtained which can be applied to hair easily without running during the period in which it is allowed to act on the hair.

Therefore, the subject matter of the invention is further a method for decoloring and bleaching hair, particularly human hair, in which 20 to 40 g, preferably 30 g, of a preparation in solid form is mixed immediately prior to use with a content of an inorganic persulfate with an aqueous solution containing 4 to 18 percent by volume of hydrogen peroxide in a weight ratio of 2:1 to 1:3, preferably 1:1.5 to 1:2. The mixture is applied to the hair, allowed to act for a period of 15 to 60 minutes and is then rinsed out with water. The method is characterized in that a preparation described in the preceding which contains persulfate in granulated form is used as preparation in solid form.

While the invention has been illustrated and described as embodied in a persulfate-containing bleaching granules, two components composition and method for using the two component composition, it is not intended to be limited to the details shown, since various modifications and structural changes may be made without departing in any way from the spirit of the present invention.

Without further analysis, the forgoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Preparation for use in a hair bleaching composition, said preparation consisting of a plurality of granule particles, each of said granule particles consisting essentially of persulfate and having a particle diameter form 0.1 to 0.6 cm, and at least one other granulated substance including granulated alkaline reacting salts selected from the group consisting of granulated alkaline reacting alkali metal salts and granulated alkaline reacting alkaline earth metal salts, said other granulated substance consisting of other granule particles having particle diameter of from about 0.1 to 0.6 cm.

2. Preparation as defined in claim 3, wherein said granule particles consisting of persulfate are present in an amount from 30 to 65% by weight.

3. Preparation as defined in claim 1, wherein said alkaline reacting salts are present in an amount from 15 to 45 percent by weight.

4. Preparation as defined in claim 1, wherein said alkaline reacting salt is selected from the group consisting of sodium carbonate, sodium silicate, sodium hydrogen carbonate and magnesium carbonate.

5. Preparation as defined in claim 1, wherein said other granulated substance includes an ethylenediamine tetraacetic acid salt as a chelating agent.

6. Preparation as defined in claim 1, wherein said other granulated substance includes 0.1 to 15 percent by weight of a member selected from the group consisting of fatty alcohol sulfates, ethoxylated fatty alcohol sulfates, alkyl sulfates, alkylbenzene sulfonates, alkyltrimethyl ammonium salts, alkyl betaines, ethoxylated fatty alcohols, ethoxylated nonylphenols, fatty acid alkanol amides and ethoxylated fatty acid esters.

7. Preparation as defined in claim 1, wherein said other granulated substance includes a water-soluble thickener selected from the group consisting of cellulose ethers including methyl cellulose, ethyl cellulose, hydroxyethyl cellulose, methylhydroxyethyl cellulose, methylhydroxypropyl cellulose and carboxymethyl cellulose; starches including corn starch; starch ethers including carboxymethyl starch, hydroxyethyl starch and methyl starch; guar gum, xanthan gum and alginates.

8. Composition for decoloring and bleaching hair containing a first component (A) and a second component (B), said second component being an aqueous solution containing 4 to 18 percent by volume hydrogen peroxide, said first component being a preparation comprising a plurality of granule particles having particle diameters from 0.1 to 0.6 cm, each of said granule particles consisting essentially of persulfate.

9. Method of decoloring and bleaching hair comprising the steps of mixing from 20 to 40 g of a preparation with an aqueous solution containing 4 to 18 percent by volume hydrogen peroxide in a weight ratio of 2:1 to 1:3 to form a hair bleaching mixture, said preparation containing a plurality of granule particles each having a particle diameter form 0.1 to 0.6 cm and consisting essentially of persulfate; applying the hair bleaching mixture to the hair; allowing the hair bleaching mixture to act for 15 to 60 minutes on the hair and then rinsing with water.

10. Method according to claim 9, wherein 30 g of said preparation are used in the mixing.

11. Method according to claim 9, wherein the weight ratio is from 1:1.5 to 1:2.

12. Preparation for use in a composition for bleaching hair consisting of
- 30 to 65 percent by weight of a plurality of granule particles, each of said particles having a particle diameter of 0.1 to 0.6 cm and consisting of persulfate;
- 15 to 45 percent of weight of an alkaline reacting salt in granulated form, said alkaline reacting salt being selected from the group consisting of sodium silicate, sodium carbonate, sodium hydrogen carbonate and magnesium carbonate;
- 0.1 to 3 percent by weight of a chelating agent selected from the group consisting of ethylenediamine tetraacetic acid salts; and
- 0.01 to 1 percent by weight of a dye selected from the group consisting of ultramarine dyestuffs and acidic dyestuffs.

13. Preparation for use in a composition of bleaching hair consisting of:
- 30 to 65 percent by weight of a plurality of granule particles, each of said granule particles having a particle diameter of 0.1 to 0.6 cm and consisting of persulfate; a water-soluble thickener selected from the group consisting of cellulose ethers including methyl cellulose, ethyl cellulose, hydroxyethyl cellulose, methylhydroxyethyl cellulose, methylhydroxypropyl cellulose and carboxymethyl cellulose; starches including corn starch; starch ethers including carboxymethyl starch; hydroxyethyl starch and methyl starch; guar gum, xanthan gum and alginates and a member selected from the group consisting of fatty alcohol sulfates, ethoxylated fatty alcohol sulfates, alkyl sulfates, alkylbenzene sulfonates, alkyltrimethyl ammonium salts, alkyl betaines, ethoxylated fatty alcohols, ethoxylated nonylphenols, fatty acid alkanol amides and ethoxylated fatty esters;
- 15 to 45 percent by weight of a plurality of other granule particles, each of said other granule particles consisting of an alkaline reacting salt selected from the group consisting of sodium silicate, sodium carbonate, sodium hydrogen carbonate and magnesium carbonate; a water-soluble thickener selected from the group consisting of cellulose ethers including methyl cellulose, ethyl cellulose, hydroxyethyl cellulose, methylhydroxyethyl cellulose, methylhydroxypropyl cellulose and carboxymethyl cellulose; starches including corn starch; starch ethers including carboxymethyl starch hydroxyethyl starch and methyl starch; guar gum, xanthan gum and alginates and an member selected from the group consisting of fatty alcohol sulfates, ethoxylated fatty alcohol sulfates, alkyl sulfates, alkylbenzene sulfonates, alkyltrimethyl ammonium salts, alkyl betaines, ethoxylated fatty alcohols, ethoxylated nonylphenols, fatty acid alkanol amides and ethoxylated fatty acid esters;
- 0.1 to 3 percent by weight of a chelating agent selected from the group consisting of ethylenediamine tetraacetic acid salts; and
- 0.01 to 1 percent by weight of a dye selected from the group of ultramarine dyestuffs and acidic dyestuffs,
wherein said preparation contains the water-soluble thickener in an amount of 0.1 to 15 percent by weight and said member in an amount of 0.1 to 15 percent by weight.

* * * * *